United States Patent [19]

Augstein

[11] Patent Number: 5,686,047
[45] Date of Patent: Nov. 11, 1997

[54] EVALUATION INSTRUMENT FOR TEST STRIPS WITH A TRANSPORT UNIT FOR TEST STRIPS

[75] Inventor: Manfred Augstein, Mannheim, Germany

[73] Assignee: Boehringer Mannheim GmbH, Mannheim, Germany

[21] Appl. No.: 503,693

[22] Filed: Jul. 18, 1995

[30] Foreign Application Priority Data

Jul. 19, 1994 [DE] Germany ............ 44 25 439.3

[51] Int. Cl.⁶ .................... G01N 35/04; G01N 21/13
[52] U.S. Cl. .................. 422/65; 422/63; 422/66; 436/43; 436/44; 436/46; 436/48
[58] Field of Search ................ 422/62, 65, 66, 422/67, 104; 436/43, 44, 46, 807, 809, 48

[56] References Cited

U.S. PATENT DOCUMENTS

| | | |
|---|---|---|
| 3,645,690 | 2/1972 | Rochte et al. ............ 422/65 |
| 3,918,910 | 11/1975 | Soya et al. . |
| 4,257,862 | 3/1981 | Schnipelsky et al. ........ 204/195 |
| 4,269,803 | 5/1981 | Jessop .................. 422/63 |
| 4,689,202 | 8/1987 | Khoja et al. ............. 422/65 |
| 4,826,659 | 5/1989 | Akisada ................ 422/63 |
| 4,876,204 | 10/1989 | Inoue et al. ............ 436/46 |
| 5,039,615 | 8/1991 | Takahata ............... 436/44 |
| 5,143,694 | 9/1992 | Schafer et al. ........... 422/65 |
| 5,384,094 | 1/1995 | Schacher ............... 422/64 |

FOREIGN PATENT DOCUMENTS

| | | |
|---|---|---|
| 0 216616 A2 | 4/1987 | European Pat. Off. . |
| 0 431455 A2 | 6/1991 | European Pat. Off. . |

*Primary Examiner*—Long V. Le
*Attorney, Agent, or Firm*—Nikaido, Marmelstein, Murray & Oram LLP

[57] ABSTRACT

The invention lies in the field of analyzing sample liquids with the aid of test strips and addresses an evaluation instrument for test strips where test strips are transported by a grabber. The grabber is attached to a guide arm that is moved in one spatial direction. A redirecting mechanism serves to apply the movement of the guide arm to the grabber such that a movement in at least two spatial directions is carried out.

10 Claims, 4 Drawing Sheets

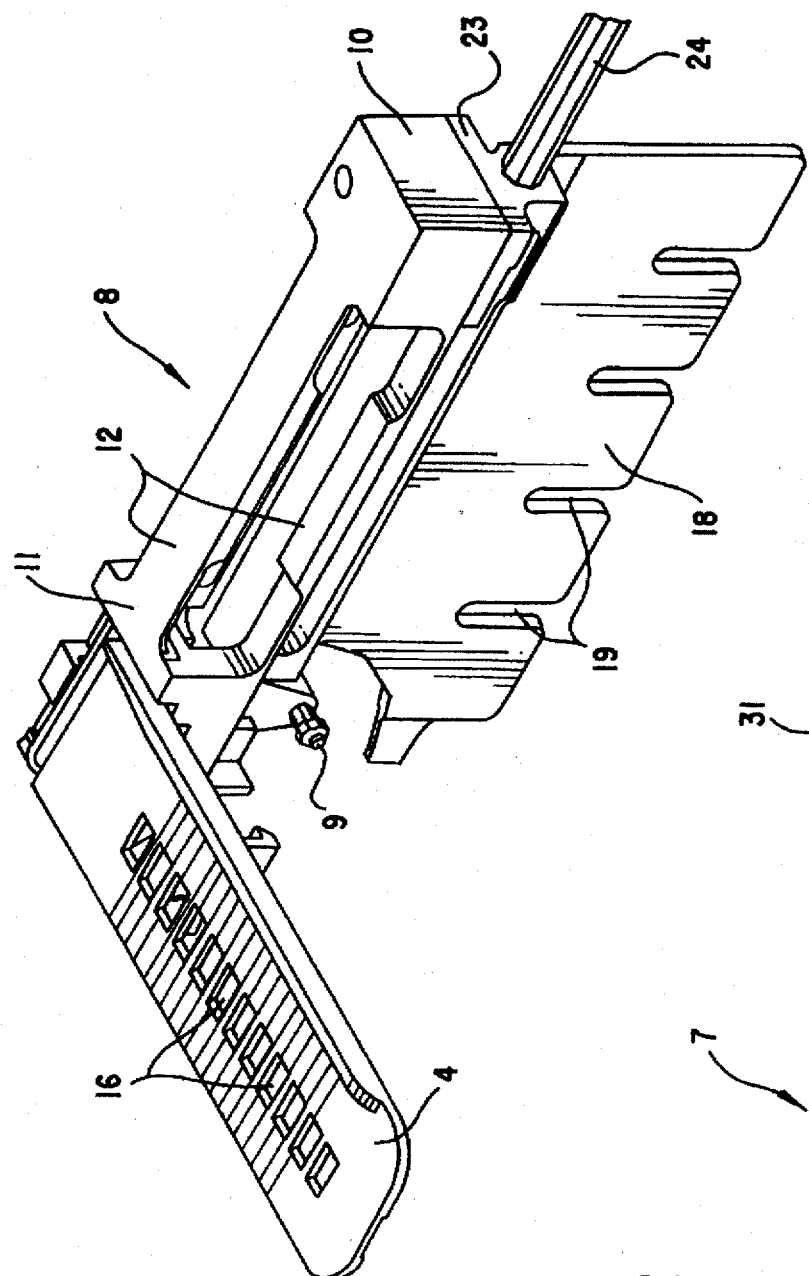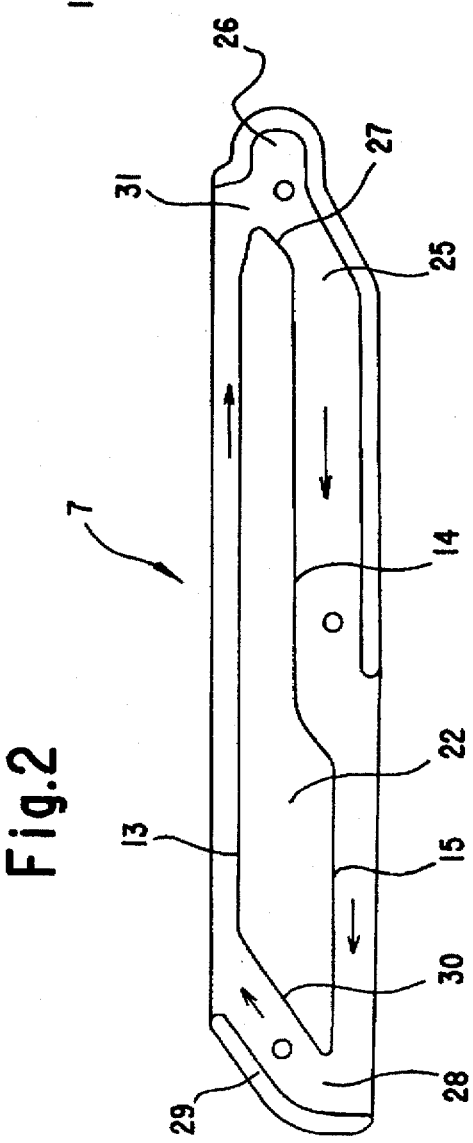

EVALUATION INSTRUMENT FOR TEST STRIPS WITH A TRANSPORT UNIT FOR TEST STRIPS

The invention addresses an instrument for evaluating test strips. The instrument has a transport unit where a grabber transports test strips perpendicularly to their longitudinal extension over a test strip support to a measuring position and further to a disposal area. The grabber is controlled via a drive unit with a vertical profile, a guide arm, and a drive motor. Said drive motor moves the base of the guide arm in a single spatial direction. The movement of the guide arm head is redirected via a guide pin that engages the vertical profile such that the grabber which is attached to the head of the guide arm executes a movement which consists of at least two spatial directions.

The photometric evaluation of test strips is primarily used in the field of clinical analysis for testing urine, blood, and serum samples. Conventional test strips have several test fields for the determination of different sample components. Usually, the test strips are immersed into a sample liquid, excess sample liquid is wiped off, if necessary, and the strip is then inserted into an evaluation instrument. The reaction of the sample components lead to a change in the color of the test fields which is usually evaluated with the aid of a photometer, particularly with a reflectance photometer. High demands are made on the test strip evaluation instruments with respect to user friendliness and accuracy of evaluation. Correct positioning of the test fields underneath the measuring head is critical to the accuracy of the evaluation; and maintaining a defined distance between measuring head and test field surface is particularly important for the accuracy of the evaluation.

In prior art, a test strip evaluation instrument is known from patent application EP-A-0 431 455 which allows transporting and positioning test strips. With the apparatus described in this patent application, it is possible to have a step-wise transport of test strips via a synchronized movement of carrier elements and test strip support. Carrier elements and test strip support are each driven by a separate motor. Moreover, the described device is intended for the simultaneous evaluation of a multitude of test strips. The instrument is therefore little advantageous for the user when single test strips are to be evaluated. As the instrument is designed for the evaluation of a multitude of test strips, its manufacture involves correspondingly high costs.

It was, hence, an object of the invention to provide a test strip evaluation instrument that is suitable for the evaluation of individual or a small number of test strips and features at the same time a high degree of user comfort and measurement accuracy. It was a particular object of the invention to provide a transport unit for a test strip evaluation instrument that accomplishes the functions of transporting and positioning with the aid of a simple drive unit.

This object is achieved with a test strip evaluation element having a transport unit where a gabber transports the test strips perpendicularly to their longitudinal extension over a test strip support to the measuring position and further to a disposal area. The grabber is controlled via a drive unit having a vertical profile, a guide arm, and a drive motor. The drive motor moves the base of the guide arm in one spatial direction. The movement of the guide arm head is redirected via a guide pin that engages the vertical profile such that the grabber which is attached to the guide arm executes a movement that is composed of at least two spatial directions.

The present test strip evaluation instrument facilitates the evaluation of small amounts of test strips also in that transportation of test strips into the measuring position is not carded out manually, but with the aid of a transport unit. The transport unit consists of several cooperating elements. A grabber is the one element of the transport unit which is in direct contact with the test elements. The grabber in accordance with the invention has the shape of a thin plate with a length of few centimeters, a width of a few centimeters, and a thickness of a few millimeters. The grabber has integrated measuring openings through which the test fields of test elements located underneath the grabber can be accessed. Moreover, the grabber has guide elements to guide a test strip over the test strip support and to align said test strip. Possible guide elements include bars or hooks attached to the bottom of the grabber.

The grabber is attached to the head of a guide arm to which also a guide pin is attached.

A connecting element provides a flexible connection between the head of the guide arm and the base of the guide arm. Said connecting element allows a perpendicular movement of the head with respect to the test strip support. In a preferred manner, said connecting element is configured as a dual leaf spring. As compared to a single leaf spring, said dual spring has the advantage that a twisting of the guide arm head is prevented. Advantageously, head, base, and dual leaf spring can be manufactured as a single integrated element.

A drive unit moves the base of the guide arm in one spatial direction. A great number of drive units have been described for such a one-dimensional movement in prior art. It is particularly advantageous for the invention if the base of the guide arm is located on a slide that moves in a guide rail. The slide can be moved on the guide rail, for example, with the aid of a tooth rack that is linked to the slide. Owing to the special requirements made on the transport unit with respect to accuracy of positioning, it has been proven advantageous if a slotted plate is attached to the slide which can be engaged with eccentric pins of a drive motor.

This type of drive unit has specific positions where a relatively large change in the rotational angle causes only very small movements of the slotted plate and, hence, the guide arm. These specific positions can be accessed with a very high degree of accuracy, even when the drive motor operates with a relatively great positional inaccuracy. Therefore the general costs for the drive motor can be reduced.

While the guide arm is moved by the drive motor, a guide pin attached to the head of the guide arm engages the vertical profile. The vertical profile determines the vertical position of the head of the guide arm in dependency of the lateral position of the guide arm. The vertical profile is provided with a groove as a guide pin rail. The groove is preferably a closed circuit, so that the guide arm moves along the complete length of the groove during its lateral movement from a given initial position to a given end position and back. Because of the closed circuit of the groove, the guide arm and especially its head can be moved in successive cyclic movements. Owing to the connection of the base to the head of the guide arm with a leaf spring, it is possible to have a particularly simple configuration of the vertical profile. The tension of the spring serves to give the guide arm a defined direction in its vertical movement.

One possible embodiment of the vertical profile includes an essentially rectangular plastic block where a groove has been included by milling. The groove has an essentially oval shape with the longer partial sections of the oval being associated with a longer lateral movement of the guide pin and a shorter vertical movement of said pin; and the shorter, bent parts of the groove allow a strong vertical movement of the guide pin. When the guide pin runs in the described groove, a one-dimensional movement of the guide pin is partly redirected to continue in a second direction. In the apparatus described, purpose of the guide groove is to convert the lateral movement of the pin partly into a vertical movement. This mechanism, hence, serves to save a separate drive unit for the second direction of movement.

A vertical profile integrated in the instrument preferably has several levels parallel to the lateral direction of movement of the guide arm. These levels are associated with various vertical positions of the guide arm head. These different levels, hence, serve the following purposes in given positions of the guide arm:

to move the grabber so far away from the test strip support that contact of the grabber with the test strip on the test strip support is prevented, to guide the grabber at a distance above the test strip support at which it moves the test strip along to transport it into the measuring position, to press the grabber onto the test strip to ensure suitable positioning for a measurement.

Moreover, the vertical profile can have an arresting position into which the guiding pin is moved when the instrument is to be shipped or if it is out of service for an extended period of time.

The invention further includes a method for evaluating test strips in a test strip evaluation instrument, comprising the following steps:

placing a test strip onto a test strip support, transporting the test strip with the aid of a grabber in direction toward a measuring position, fixing the test strip in measuring position, photometric evaluation of the test strip, transporting the test strip into a disposal area.

The method is characterized in that the grabber is attached to a guide arm whose movement is controlled via a vertical profile while said guide arm is driven by a motor.

The invention further comprises a method for evaluating test strip in a test strip evaluation instrument, said method comprising the following steps:

placing a test strip onto a test strip support, transporting the test strip with the aid of a grabber in direction toward the measuring position, fixing the test strip in measuring position, photometric evaluation of the test strip, transporting the test strip into a disposal area.

This method is characterized in that the grabber is attached to a guide arm whose movement is controlled via a vertical profile while said guide arm is driven by a motor.

The device for evaluating test strips as described above can be used to implement said method.

Before a test strip is evaluated, the strip is usually brought into contact with a sample liquid. This is done by immersing the test strip into a sample liquid either manually or with the aid of a robot arm. It is also possible that sample liquid is applied onto the test fields of a test strip with a pipette, for example. Once the sample liquid is on the test field, any excess sample liquid may be wiped off the test strip. The so prepared test strip is then inserted into the test strip evaluation device either manually or with the aid of another device. In accordance with the invention, the test strip is placed onto a test strip support. In many test strips, a sample-induced alteration of the test strip occurs in dependency upon time. In many cases, the test strip is therefore incubated prior to evaluation on the test strip support. It is also possible to transport the test strip with the grabber for incubation to another site on the test strip support. It is thus possible to process several test strips in parallel which increases the throughput of the evaluation instrument.

For the measurement, the grabber moves the test strip across the test strip support into measuring position. The test strip is preferably transported transversely to its longitudinal axis. For an explanation of how the test strip is transported with the aid of the vertical profile, please refer to FIGS. 1 and 2 and the corresponding descriptions.

Once in measuring position, the test strip is fixed in its position by the grabber, i.e. its lateral and vertical positions are exactly set by the guide elements of the grabber. The photometric evaluation of the test strip is preferably accomplished in that a measuring head moves over the upper side of the grabber. The measuring head exerts pressure onto the arrangement of a grabber, test strip, and test strip support so as to exactly define the vertical position of the test strip. After the measurement head has moved across all the individual test fields of the test strip, it is moved away from the grabber. The now released grabber transports the test strips into a disposal area. In accordance with the invention, it is also possible that the test strip is transported into a second measuring position after the first measurement has been completed where a second measurement is then carried out. The time dependency of the detection reaction can then be determined by having duplicate or multiple measurements of the test strip.

A measuring head suitable for evaluation comprises a radiation source to expose the test fields of the strip to radiation, then a detector to detect the radiation reflected by the test fields. Possible sources of radiation are, for example, light-emitting diodes. Radiation detectors used in the practice are photodiodes or photovoltaic elements. The design of the measuring heads is commonly known from prior art.

The radiation used for the evaluation is usually in the visible range. The use of infra-red or ultraviolet radiation is, however, also possible.

BRIEF DESCRIPTION OF THE DRAWINGS

The evaluation device and especially the control of the grabber via the vertical profile is explained with reference to the following figures.

FIG. 1: guide arm of the evaluation instrument

FIG. 2: vertical profile

DETAILED DESCRIPTION OF THE DRAWINGS

Figure 3:
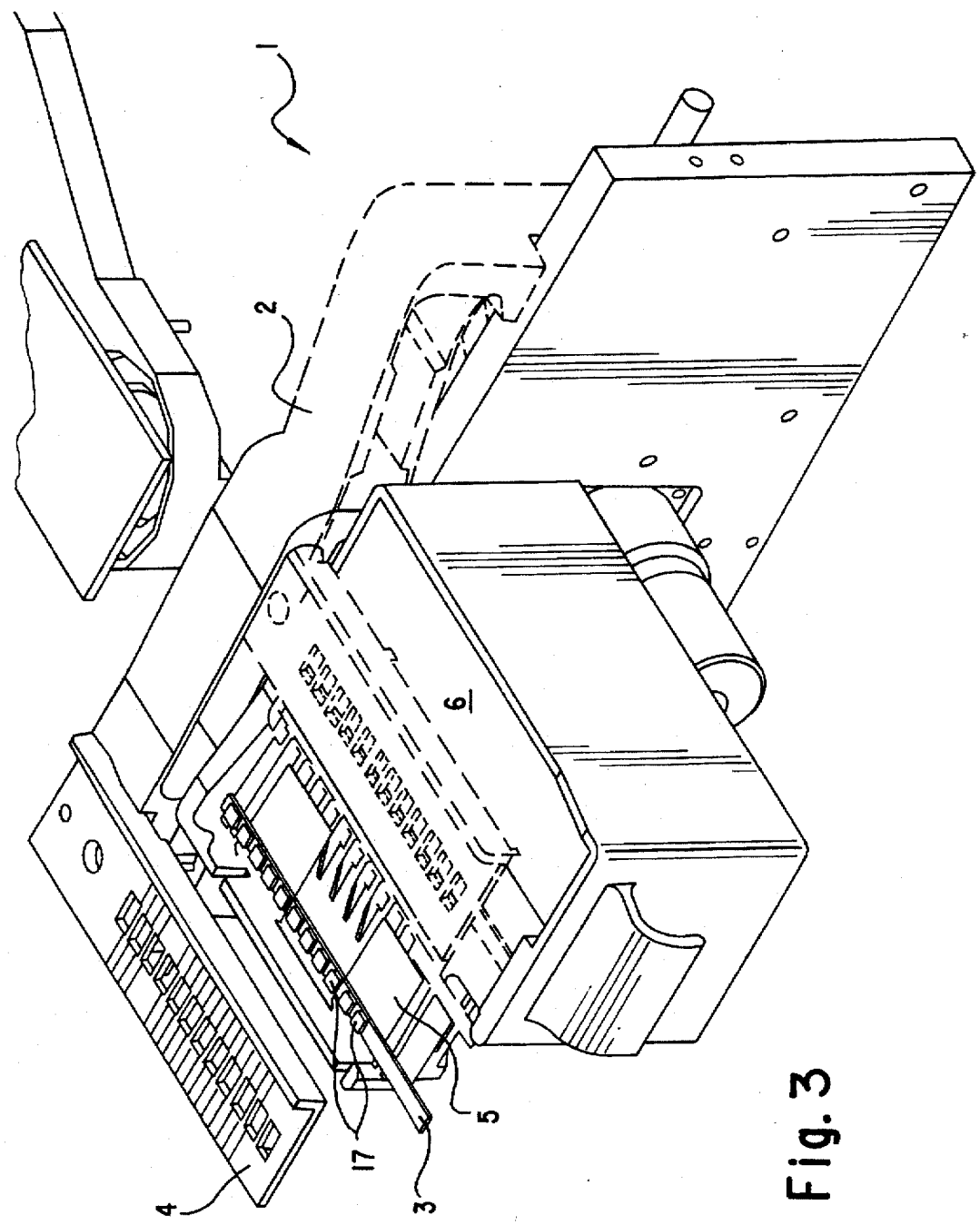
FIG. 3: top view of a test strip evaluation instrument

FIG. 1 shows the guide arm (8) of the test strip evaluation instrument (1). The guide arm (8) comprises a slide (23) running on a guide rail (24). A motor engaging the slots (19) in the slotted plate (18) moves the entire guide arm (8) on the guide rail (24) in one spatial direction. Slotted plate (19) and base (10) of the guide arm are rigidly connected to slide (23). A dual leaf spring (12) flexibly connects base (10) of the guide arm to head (11) of the guide arm so as to move head (11) of the guide arm perpendicularly to the moving direction of the guide arm (8) within the limits set by the leaf spring. A guide pin (9) engaging the vertical profile is provided at head (11) of the guide arm. Grabber (4) is connected to head (11) via a snap connection. The grabber has measuring openings (16) through which the test fields of a strip located under the grabber (4) can be accessed.

FIG. 2 shows a vertical profile (7) with a profile (22) with three parallel levels (13, 14, 15). If guide arm (8) is moved on guide rail (24), guide pin (9) runs in groove (25).

An evaluation cycle is now described as an example with respect to FIG. 2:

When the instrument is prepared for operation, guide pin (9) is usually in its initial position (26). This corresponds to a position of grabber (4) where there is no contact made with the test strip support. The guide arm is now moved into direction toward the measuring position, while the guide pin moves toward profile (22) while being redirected by slanted portion (27) to arrive at area (14). If the guide pin now moves over area (14), test strip support and grabber are at a distance in which the guide elements of the grabber carry the test strip along. If the guide pin continues to move in direction of the arrow, it travels along a curved section to reach area (15). When moving on this level, grabber and test strip support are in contact, i.e. the test strip located between grabber and test strip support is pressed onto the test strip support. Correspondingly, a portion of area (15) is associated with the measuring position. When the measurement is completed, the guide arm and, hence, the guide pin continue to move in direction of the arrow to reach a reverse position (28). Because of the action of the dual leaf spring (12), the head of the guide arm and, hence, the guide pin are moved upwardly, i.e. against reversing rail (29). The revese position (28) coincides with the reversal of the direction of movement of the guide arm on the guide rail. Now, the guide pin moves via a second slanted portion (30) toward level (13). Level (13) corresponds to a relatively large distance between grabber and test strip support where a test strip located on the test strip support is not in contact with the guide elements of the grabber. On level (13) the grabber returns to its initial position to process another test strip. If the guide pin arrives at the second reversing position (31), the head of the guide arm, as a consequence of the spring action of the dual leaf spring, is urged it into arresting position (26). Another cycle of movement can now start at this position.

An advantage of the embodiment described above is that the path of the guide pin (9) in the vertical profile (7) is closed so as to allow a cyclic movement of successive evaluation cycles.

The relatively simple guidance of the grabber via the vertical profile is also a result of the fact that at the return position, the direction of movement of the guide pin is clearly set because of the spring tension of the dual leaf spring (12). On levels (13, 14, 15), the spring acts such that it presses the guide pin (9) against profile (22). Slanted areas (27, 30) and also the curved section between levels (14, 15) serve to generate a spring tension. Arresting position (26) is also approximately the resting position of the spring.

FIG. 3 is a top view of test strip evaluating instrument (1). In this representation, grabber (4) is in arresting position (26). A test strip (3) with test fields (17) is located on the test strip support. From the drawing it can be understood that the test strip support (5) has planar surfaces, but also cross bars and grooves. When a test strip is transported across the test strip support, the grabber is lowered over the test strip support such that the guide elements of the grabber engage the grooves on the test strip support. It is thus possible to have a simple and damage-free transport of the test strips.

The broken lines in FIG. 3 indicate the position of grabber (4) and transport unit (2) in the measuring position. The disposal area (6) is also indicated behind the measuring position.

Figure 4:
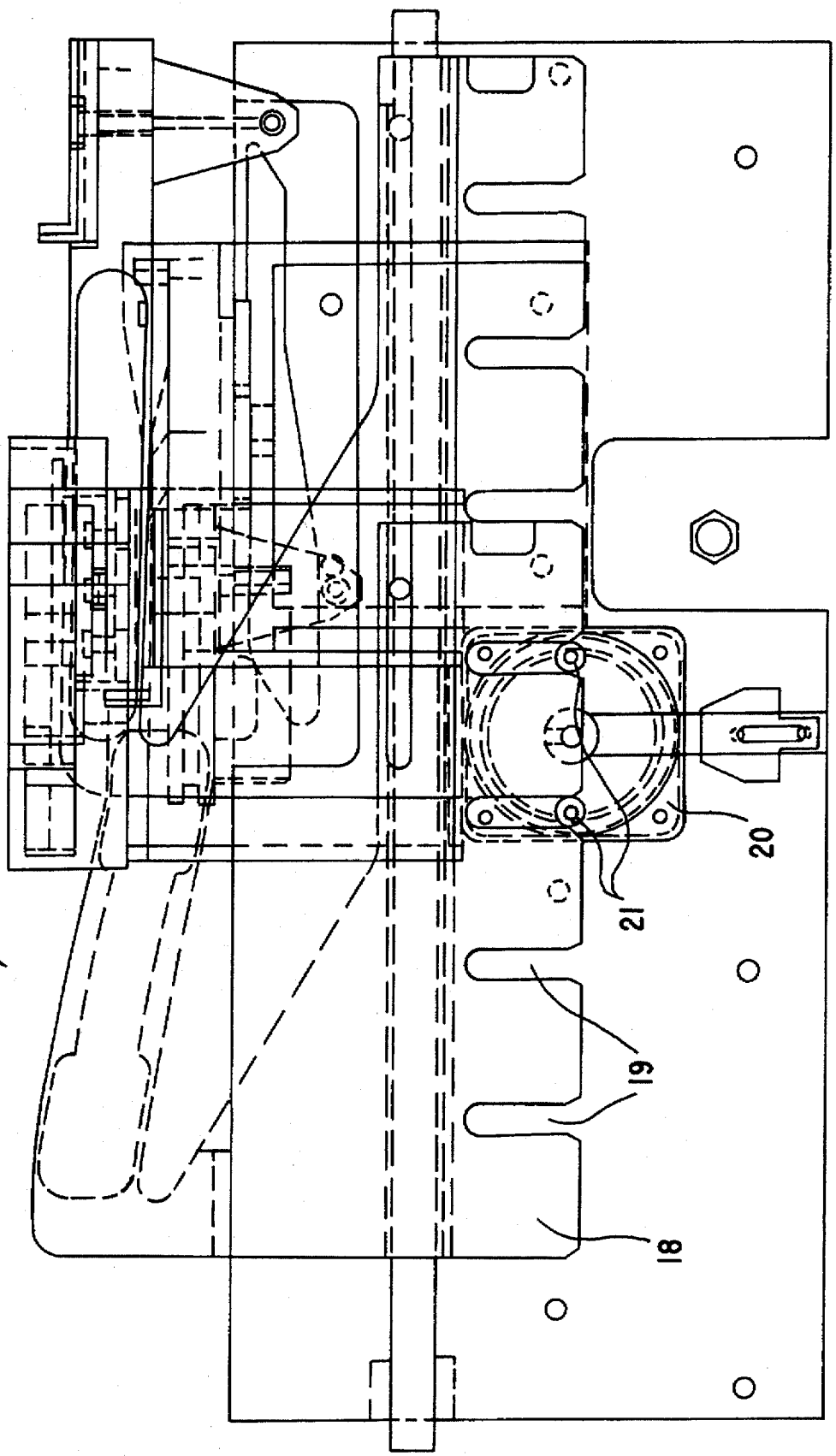
FIG. 4: lateral view of the test strip evaluation instrument

FIG. 4 is a lateral view of test strip evaluation instrument (1). The figure shows in particular how the guide arm is moved via slotted plate (18). Drive motor (20) has a rotary disc to which two eccentric pins (21) are attached. Said eccentric pins (21) engage the slots (19) in slotted plate (18). In the position shown, a relatively large rotation of the motor corresponds to a relatively small movement of the slotted plate (19) and, hence, the guide arm. While the motor continues to move into a position rotated by 90°, the ratio between displacement of the slotted plate and rotating angle of the motor increases.

Figure 5:
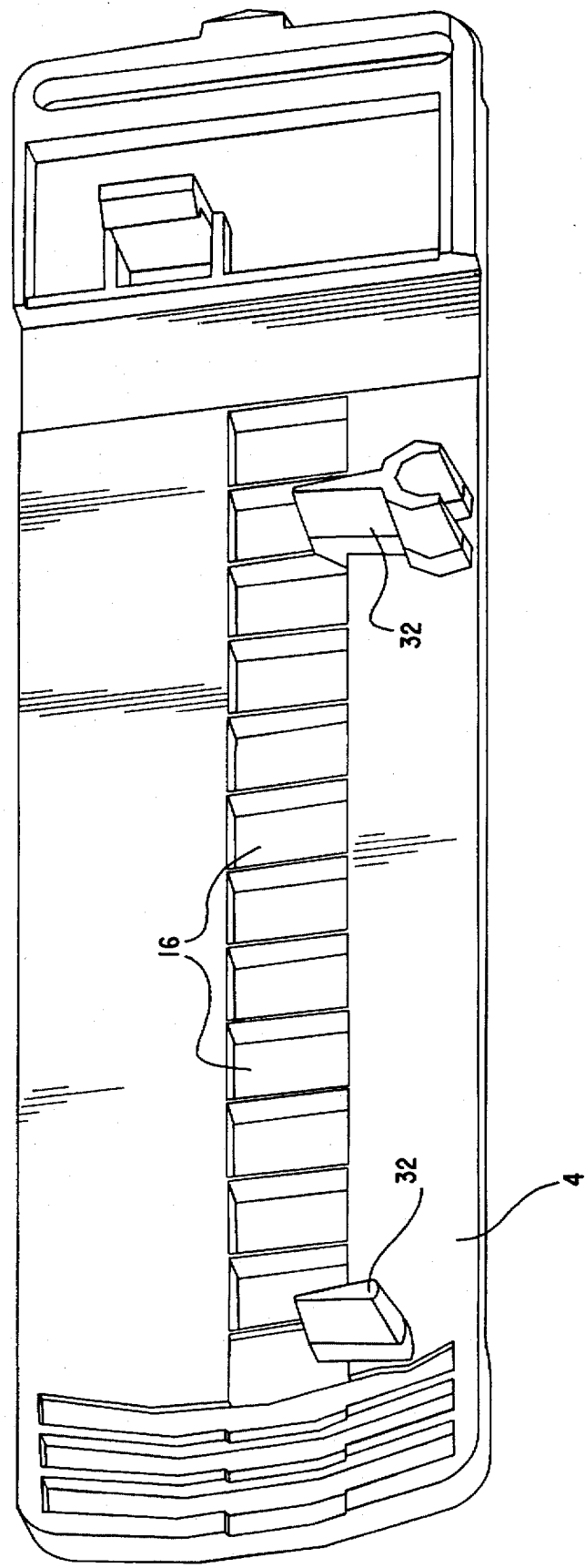
FIG. 5: view of the lower side of the grabber.

The selected positions which can be adjusted with great accuracy due to the described transmission ratio of rotating angle to linear movement are selected by choosing a suitable arrangement of relative position of motor and slotted plate and/or distance of the eccentric pins (21). One selected position is in particular the measuring position. FIG. 5 is a view of the lower side of the grabber (4). The figure shows measuring openings (16) and in particular the guide elements (32). If grabber (4) carries a test element along on the test strip support, the test element is located transversely in front of the guide elements (32) so that test fields of the test element come to rest opposite the measuring openings (16). In case a test strip is not located straight on the test strip support initially, it is urged against the guide elements (32) when taken along by the grabber. The test strips then assume a defined orientation with respect to the measurement openings (16).

For information regarding a related invention, reference should be made to a patent application entitled "Device for the Reflectometric Evaluation of Test Elements", invented by Mr. Manfred Augstein, filed on even date herewith, and given U.S. patent application Ser. No. 08/503,695.

List of Reference Numerals (1) Test strip evaluation instrument
(2) Transport unit
(3) Test strip
(4) Grabber
(5) Test strip support
(6) Disposal area
(7) Vertical profile
(8) Guide arm
(9) Guide pin
(10) Base of guide arm
(11) Head of guide arm
(12) Dual leaf spring
(13) First level
(14) Second level
(15) Third level
(16) Measuring openings
(17) Test fields
(18) Slotted plate
(19) Slots
(20) Drive motor
(21) Eccentric pins
(22) Profile
(23) Slide
(24) Guide rail
(25) Groove
(26) Arresting position
(27) Slanted portion
(28) Reverse position
(29) Reversing rail
(30) Second slanted portion
(31) Second reverse position
(32) Guide elements

I claim:

1. A test strip evaluation instrument for transporting and supporting test strips for evaluation and disposal thereof, said evaluation instrument comprising:

a test strip support on which a test strip is supported;

grabbing means for engaging the test strip and moving the test strip on the test strip support;

drive means coupled to said grabbing means for moving said grabbing means in a predetermined path, said drive means including a drive motor for moving said grabbing means;

path means for providing the predetermined path for said grabbing means;

a guide means coupled to said grabbing means for supporting said grabbing means, said guide means including a guide pin for engaging said path means for guiding said grabbing means along said predetermined path, wherein said guide means includes a base which is coupled to said drive motor such that said guide pin engages said path means such that said path means directs a movement of said guide means whereby the grabbing means is moved along said predetermined path in at least two spatial directions, and wherein the test strip is moved on the test strip support by the grabbing means into a measuring position, and then subsequently moved by the grabbing means into a disposal area.

2. A test strip evaluation instrument as recited in claim 1, said guide means further comprising a head thereof having the grabbing means connected thereto, said head being connected to said base by a spring means.

3. A test strip evaluation instrument as recited in claim 2, wherein said spring means comprises a leaf spring.

4. A test strip evaluation instrument as recited in claim 2, wherein said spring means comprises dual leaf springs.

5. A test strip evaluation instrument as recited in claim 1, further comprising a test strip support for supporting test strips thereupon, wherein said path means comprises a vertical profile having three vertical levels, and wherein a first level defines a distance between said grabbing means and said test strip support, a second level defines a level whereby the grabbing means engages and transports a test strip over said test strip support, and wherein a third level of said vertical profile defines a level wherein said grabbing means supports a test strip in a measuring position on said test strip support.

6. A test strip evaluation instrument as recited in claim 5, wherein said path means defines said levels by a closed movement path of said guide pin.

7. A test strip evaluation instrument as recited in claim 5, wherein the path means moves said guide pin in a direction toward the test strip support at said first level, and away from the test strip support at said third level, said guide pin being guided through said predetermined path of said guide means by a biasing force of a spring means connected to said guide means.

8. A test strip evaluation instrument as recited in claim 1, wherein said grabbing means includes guide elements for engaging and guiding the test strip.

9. A test strip evaluation instrument as recited in claim 1, wherein said grabbing means includes a plurality of measuring openings therein, said plurality of measuring openings corresponding to a plurality of test fields of said test strip.

10. A test strip evaluation instrument as recited in claim 1, said base further comprising a slotted plate attached to said guide means, said slotted plate being configured to engage eccentric pins driven by said drive motor.

* * * * *